United States Patent [19]

Etzbach

[11] Patent Number: 4,814,465

[45] Date of Patent: Mar. 21, 1989

[54] PREPARATION OF AMINOTHIOPHENE DERIVATIVES

[75] Inventor: Karl-Heinz Etzbach, Frankenthal, Fed. Rep. of Germany

[73] Assignee: Basf Aktiengesellschaft, Ludwigshafen, Fed. Rep. of Germany

[21] Appl. No.: 84,833

[22] Filed: Aug. 13, 1987

[51] Int. Cl.$^4$ .................. C07D 333/38; C07D 333/32; C07D 333/36

[52] U.S. Cl. ........................................ 549/61; 549/62; 549/68; 549/69

[58] Field of Search ........................ 549/61, 62, 68, 69

[56] References Cited

FOREIGN PATENT DOCUMENTS 3529831  3/1986  Fed. Rep. of Germany ...... 534/573
3517365 11/1986  Fed. Rep. of Germany ...... 534/573

OTHER PUBLICATIONS

Nippon Kayaku Co., CA vol. 96, 1982 96: 87016p, p. 80.
Mittelbach et al., CA vol. 104, Jun. 9, 1986, 104: 206695e.
Baird et al., CA, vol. 84, 1976, 84: 135461f, p. 480.
Schefczik et al., CA, vol. 106, 1987, 106: 139827a, p. 80.

*Primary Examiner*—Alan L. Rotman
*Attorney, Agent, or Firm*—Oblon, Fisher, Spivak, McClelland & Maier

[57] ABSTRACT

Aminothiophene derivatives of the formula I

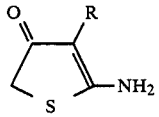

where R is unsubstituted or substituted $C_1$-$C_8$-alkyoxycarbonyl, unsubstituted or substituted carbamyl or cyano, are prepared by a process in which a compound of the formula II

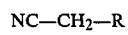

where R has the above meanings, is reacted in water with a base and simultaneously or subsequently with a haloacetyl halide, and the product is then reacted with hydrogen sulfide or a water-soluble sulfide.

8 Claims, No Drawings

PREPARATION OF AMINOTHIOPHENE DERIVATIVES

The present invention relates to a process for the preparation of aminothiophene derivatives of the formula I

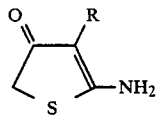   (I)

where R is $C_1$–$C_8$-alkoxycarbonyl whose alkyl chain may be interrupted by one or more oxygen atoms, carbamyl, $C_1$–$C_4$-mono- or dialkylcarbamyl which is unsubstituted or substituted by hydroxyl or $C_1$–$C_4$-alkoxy, or phenylcarbamyl or cyano, wherein a compound of the formula II

NC—CH$_2$—R   (II), where R has the above meanings, is reacted in water with a base and simultaneously or subsequently with a haloacetyl halide, and the product is then reacted with hydrogen sulfide or a water-soluble sulfide.

All alkyl groups occurring in the formulae I and II may be either straight-chain or branched.

R is, for example, COOCH$_3$, COOC$_2$H$_5$, COO$_3$H$_7$, COOC$_4$H$_9$, COOC$_5$H$_{11}$, COOC$_6$H$_{15}$, COOC$_7$H$_{15}$, COOC$_8$H$_{17}$,

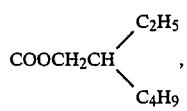

COOCH$_2$CH$_2$OCH$_3$, COOC$_2$H$_4$OC$_2$H$_5$, CONH$_2$, CONH$_2$, CONHC$_2$H$_5$, CONHC$_3$H$_7$, CONHC$_4$H$_9$, CONHC$_6$H$_5$, CONHC$_2$H$_4$OH, CONHC$_2$H$_4$OCH$_3$, CON(CH$_3$)$_2$, CON(C$_2$H$_5$)$_2$, CON(C$_3$H$_7$)$_2$, CON(C$_4$H$_9$)$_2$ or CON(C$_2$H$_4$OCH$_3$)$_2$. R is preferably cyano.

Examples of bases which are suitable for the reaction are amines or hydroxides, carbonates or bicarbonates of alkali metals or alkaline earth metals.

Specific examples of bases are trimethylamine, triethylamine, tripropylamine, tributylamine, tri-(2-hydroxyethyl)-amine, tri-(2-hydroxypropyl)-amine, pyridine, magnesium, calcium, strontium, barium, lithium, sodium and potassium hydroxide, lithium, sodium and potassium carbonate and lithium, sodium and potassium bicarbonate.

The carbonates are particularly preferred, especially potassium carbonate.

Haloacetyl halides are, in particular, the chlorine and bromine compounds, chloroacetyl chloride being preferred for economic reasons.

Particular examples of soluble sulfides are alkali metal sulfides, ammonium sulfide and the corresponding hydrogen sulfides. Hydrogen sulfide, ammonium sulfide or sodium or potassium hydrogen sulfide is preferably used.

The process according to the invention is advantageously carried out by initially taking 2 moles of the base per mole of the compound of the formula II in water and then slowly adding the compound II and simultaneously or, preferably, subsequently chloroacetyl chloride. Not less than 1 mole of chloroacetyl chloride, preferably an excess, is used, the amounts in each case being based on one mole of the compound of the formula II.

In the novel process, the reaction temperature is preferably from 0° to 20° C. Inert solvents, such as N,N-dimethylformamide, N-methylpyrrolidone, methanol, ethanol, isopropanol, butanol, butylglycol, chloroform, methylene chloride, 1,1,1-trichloroethane, 1,1,2-trichloroethane, toluene, xylene, chlorobenzene, nitrobenzene, ethyl acetate or diethyl ether, and phase transfer catalysts, such as tetrabutylammonium bromide, tricaprylmethylammonium chloride, benzyltrimethylammonium chloride, benzyltriethylammonium chloride, (2-hydroxyethyl)-triethylammonium chloride or hexadecyltributylphosphonium bromide, may also be added to the reaction mixture. However, this is not essential.

The reaction with the sulfur compound is carried out after the first reaction at about 0°–40° C., an equivalent amount or an excess of the sulfur compound being used, the amounts in each case being based on the compound II. The aminothiophene derivatives are generally precipitated from the reaction mixture and can be isolated by a conventional method.

The aminothiophene derivatives of the formula I are obtained by the novel process in good yield and purity. They serve as intermediates, for example for diazo components of the formula III

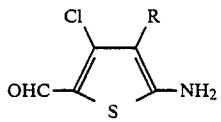   (III)

where R has the above meanings, which can be used to prepare useful disperse dyes (cf. for example DE-A-3 529 831 or DE-A-3 517 365).

The Examples below illustrate the invention. Parts and percentages are by weight, unless stated otherwise.

EXAMPLE 1

33 parts of malodinitrile were added to a mixture of 250 parts of water, 250 parts of ice and 152 parts of potassium carbonate. The mixture was stirred for 1 hour at 0° C., after which 67.4 parts of chloroacetyl chloride were added dropwise while cooling with ice, and stirring was continued for a further 2 hours at 0° C. Thereafter, 18.7 parts of hydrogen sulfide were passed into the stirred suspension at 0° C., the mixture was allowed to reach room temperature and stirred for a further 2 hours at this temperature, and the precipitate was filtered off under suction. The product was washed with water and dried at 70° C. in a through-circulation drier.

31 parts (44% of theory) of 2-amino-3-cyano-4-hydroxythiophene were obtained.

Mp. 300° C., IR (KBr): 3260, 3061 (NH$_2$), 2219 (C≡N), 1668, 1641 cm$^{-1}$ (C=O).

EXAMPLE 2

A solution of 33 parts of malodinitrile in 100 parts of N,N-dimethylformamide was added to a mixture of 250 parts of water, 250 parts of ice and 152 parts of potassium carbonate. The procedure described in Example 1 was then followed.

48 parts (69% of theory) of 2-amino-3-cyano-4-hydroxythiophene were obtained.

EXAMPLE 3

33 parts of malodinitrile were added to a mixture of 250 parts of methylene chloride, 500 parts of water and 138 parts of potassium carbonate at 0° C., and the mixture was stirred for 1 hour at 0° C. Thereafter, 56.6 parts of chloroacetyl chloride were added dropwise while cooling with ice, and stirring was continued for a further 2 hours at 0° C. 18.7 parts of hydrogen sulfide were then passed into the stirred mixture while cooling with ice, the mixture was allowed to reach room temperature and was stirred for a further 2 hours at this temperature, and the precipitate was filtered off under suction. The product was washed with water and dried at 70° C. in a through-circulation drier. 44 parts (63% of theory) of 2-amino-3-cyano-4-hydroxythiophene were obtained.

EXAMPLE 4

The procedure described in Example 3 was followed, except that, in addition to the potassium carbonate, 3 parts of tricaprylmethylammonium chloride were also added.

51 parts (73% of theory) of 2-amino-3-cyano-4-hydroxythiophene were obtained.

I claim:

1. A process for the preparation of an aminothiophene derivative of the formula:

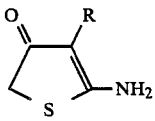

wherein R is a $C_1$–$C_8$-alkoxycarbonyl whose alkyl chain may be interrupted by one or more oxygen atoms, carbamyl, $C_1$–$C_4$-mono- or dialkylcarbamyl which is unsubstituted or substituted by hydroxyl or $C_1$–$C_4$-alkoxy, or phenylcarbamyl or cyano, comprising:
   reacting a compound of the formula: NC—$CH_2$—R wherein R is as defined above, in water containing a base simultaneously or subsequently with a haloacetyl halide; and then,
   reacting the product with hydrogen sulfide or a water-soluble sulfide.

2. The process of claim 1, wherein said nitrile compound is malodinitrile.

3. The process of claim 1, wherein the reaction of said nitrile compound with haloacetyl halide is conducted at a temperature from 0° to 20° C.

4. The proess of claim 1, wherein the base is a carbonate.

5. The process of claim 1, wherein not less than 1 mole of haloacetyl halide compound is reacted per mole of said nitrile compound in said aqueous solution containing not less than 2 moles of said base.

6. The process of claim 1, wherein said haloacetyl halide compound is chloroacetyl chloride.

7. The process of claim 1, wherein the R group of said thiophene compound is selected from the group consisting of $COOCH_3$, $COOC_2H_5$, $COO_3H_7$, $COOC_4H_9$, $COOC_5H_{11}$, $COOC_6H_{15}$, $COOC_7H_{15}$, $COOC_8H_{17}$, $COOCH_2CH(C_2H_5)(C_4H_9)$, $COOCH_2CH_2OCH_3$, $COOC_2H_4OC_2H_5$, $CONH_2$, $CONHC_2H_5$, $CONHC_3H_7$, $CONHC_4H_9$, $CONHC_6H_5$, $CONHC_2H_4OH$, $CONHC_2H_4OCH_3$, $CON(CH_3)_2$, $CON(C_2H_5)_2$, $CON(C_3H_7)_2$, $CON(C_4H_9)_2$ and $CON(C_2H_4OCH_3)_2$.

8. The process of claim 1, wherein said base is an amine, hydroxide, carbonate or bicarbonate of an alkali metal or alkaline earth metal.

* * * * *

UNITED STATES PATENT AND TRADEMARK OFFICE
CERTIFICATE OF CORRECTION

PATENT NO.    : 4,814,465
DATED         : Mar. 21, 1989
INVENTOR(S)   : Karl-Heinz ETZBACH It is certified that error appears in the above-identified patent and that said Letters Patent is hereby corrected as shown below:

The following Foreign Application Priority Data should appear on the Title page:

Sep. 4, 1986 [DE]  Fed. Rep. of Germany............3630070

Signed and Sealed this

Twenty-third Day of January, 1990

*Attest:*

JEFFREY M. SAMUELS

*Attesting Officer*      *Acting Commissioner of Patents and Trademarks*